(12) United States Patent
De Pater et al.

(10) Patent No.: US 9,006,391 B2
(45) Date of Patent: Apr. 14, 2015

(54) METHOD FOR THE PREPARATION OF CYCLOPEPTIDES

(75) Inventors: Robertus Mattheus De Pater, Delft (NL); Dhiredj Chandre Jagesar, Leiden (NL); Thomas Van Der Does, Wilnis (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 650 days.

(21) Appl. No.: 13/264,064

(22) PCT Filed: May 6, 2010

(86) PCT No.: PCT/EP2010/056147
§ 371 (c)(1),
(2), (4) Date: Oct. 12, 2011

(87) PCT Pub. No.: WO2010/128096
PCT Pub. Date: Nov. 11, 2010

(65) Prior Publication Data
US 2012/0059146 A1 Mar. 8, 2012

(30) Foreign Application Priority Data
May 7, 2009 (EP) .................. 09159630

(51) Int. Cl.
C07K 7/50 (2006.01)
C07K 7/56 (2006.01)

(52) U.S. Cl.
CPC .................. C07K 7/56 (2013.01)

(58) Field of Classification Search
USPC ............... 530/317, 333, 335, 329
IPC ........... C07K 1/02,1/061, 1/065, 5/12, 7/50
See application file for complete search history.

(56) References Cited

U.S. PATENT DOCUMENTS 5,936,062 A  8/1999 Leonard et al.
7,214,768 B2 * 5/2007 Belyk et al. .................. 530/317

OTHER PUBLICATIONS

Lowry & Richardson (Mechanism & Theory in Organic Chemistry, pp. 60-71, 1976; Harper & Row).*
International Search Report for PCT/EP2010/056147, mailed Jul. 2, 2010.
Leonard, William R. Jr. et al., "Synthesis of the antifungal beta-1,3-glucan synthase inhibitor Cancidas (caspofungin acetate) from pneumocandin B-0", Journal of Organic Chemistry, vol. 72, No. 7, (Mar. 2007), pp. 2335-2343.
Greene, T.W. Ed et al., "Chapter 2—Passage: Cyclic Bonorates", Protective Groups in Organic Synthesis Ed. 4, (2007), pp. 363-366.
Li, G. et al., "Application of 1,2:5,6-di-O-cyclohexylidene-d-mannitol as the chiral director in Matteson's asymmetric homologation", Journal of Organometallic Chemistry, vol. 581, No. 1-2, (Jun. 5, 1999), pp. 66-69.
Brooks, et al., "The Mass Spectral of Some Corticosteroid Boronates", Organic Mass Spectrometry, vol. 5, (1971), pp. 1429-1453.

* cited by examiner

*Primary Examiner* — David Lukton
(74) *Attorney, Agent, or Firm* — Nixon & Vanderhye P.C.

(57) ABSTRACT

The present invention relates to a method for preparing cyclopeptides by means of protection with a substituted boronic acid. The present invention also discloses novel boronate esters of cyclopeptides of general formula (8).

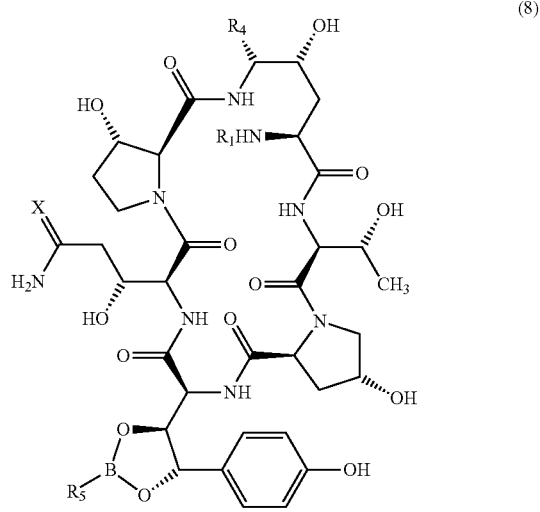

3 Claims, No Drawings

METHOD FOR THE PREPARATION OF CYCLOPEPTIDES

This application is the U.S. national phase of International Application No. PCT/EP2010/056147, filed 6 May 2010, which designated the U.S. and claims priority to EP Application No. 09159630.4, filed 7 May 2009, the entire contents of each of which are hereby incorporated by reference.

FIELD OF THE INVENTION

The present invention relates to novel cyclopeptides and to a method for preparing cyclopeptides using substituted boronic acids.

BACKGROUND OF THE INVENTION

Cyclopeptides are polypeptides in which the terminal amine and carboxyl groups form an internal peptide bond. Several cyclopeptides are known for their advantageous medicinal properties. An excellent example of this is the class of echinocandins which are potent antifungals. Cyclopeptides can be naturally occurring compounds but may also be obtained by total synthesis or by synthetic or genetic modification of naturally occurring or produced precursors; the latter class is referred to as semi synthetic cyclopeptides. Examples of medicinally useful echinocandins are the cyclic hexapeptides anidulafungin, caspofungin, cilofungin and micafungin which are useful in treating fungal infections especially those caused by *Aspergillus, Blastomyces, Candida, Coccidioides* and *Histoplasma*. Anidulafungin, caspofungin and micafungin are all semi synthetic cyclopeptides derivable from naturally occurring echinocandins such as for instance echinocandin B, pneumocandin $A_0$ or pneumocandin $B_0$.

Although nature can provide a substantive part of the complex chemical structure of semi synthetic cyclopeptides, and in many cases having all chiral centers in the required configuration, the subsequent chemical conversions into the therapeutically active derivatives nevertheless often require unprecedented approaches. Usually the structures in question are chemically unstable and/or prone to racemization and simply do not allow for otherwise obvious synthetic manipulation taught in synthetic organic chemical textbooks. This chemical instability is even more pronounced in anidulafungin, caspofungin and micafungin due to the presence of the notoriously fragile hemiaminal moiety.

The preparation of caspofungin (1) from fermentatively obtained pneumocandin $B_0$ (2), with $R_1=C(O)(CH_2)_8CH(CH_3)CH_2CH(CH_3)CH_2CH_3$ in both compounds, may serve as an example of the complexity in cyclopeptide chemistry described above.

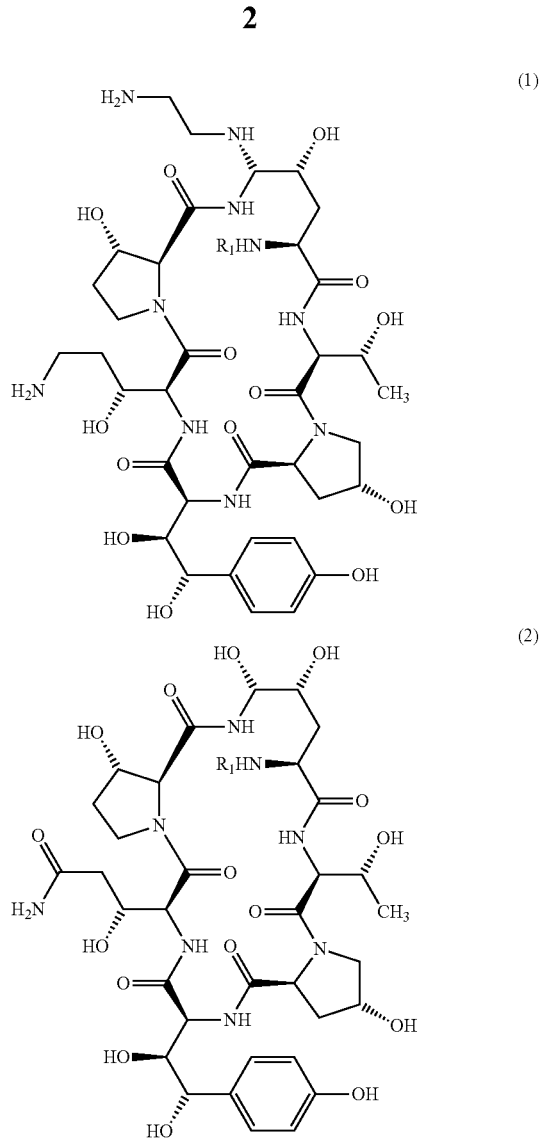

Initially, in U.S. Pat. No. 5,378,804 a process was disclosed requiring five steps and having major drawbacks in lack of stereo selectivity and an overall yield of less than 10%. The conversion of the amide functionality in (2) into the amine as present in (1) required two steps, namely dehydration of the primary amide to the nitrile followed by reduction to the amine. Introduction of the ethylenediamine moiety at the hemiaminal position required three steps. An improved procedure was disclosed in U.S. Pat. No. 5,552,521 requiring three steps in total, namely reduction of the amide followed by activation with thiophenol and stereoselective displacement of the thiophenol function to introduce the ethylenediamine moiety. Still this process suffers from a low overall yield of no more than 25%. A further improvement in yield was realized in U.S. Pat. No. 5,936,062 describing intermediate protection of, amongst others, the vicinal hydroxyl groups of the homotyrosine moiety using phenylboronic acid. Two synthetic approaches were suggested, the first one starting with phenylboronic acid protection followed by reduction with borane and activation with thiophenol and the second one starting with thiophenol activation followed by phenylboronic acid protection and reduction with borane. Both approaches were completed by introduction of the ethylenediamine moiety and overall yields ranging from 25-36% were reported. In the first approach the claimed sequence of steps involved the presence of a diboronate ester intermediate. An alternative approach to this was described by W. R. Leonard et al. (J. Org. Chem. 2007, 72, 2335-2343) involving the initial formation of a mono-phenylboronate ester protection of the vicinal hydroxyl groups allowing for immediate introduction of the thiophenol activating group. This latter approach resulted in a 45% overall yield.

Today there are no convenient alternatives to the above approaches so there remains a challenge for finding alternative chemical approaches that allow for conversion of naturally occurring cyclopeptides into semi synthetic cyclopeptides. These approaches can be used as alternative to prior art methods, or preferably to achieve a higher yield, higher chemical purity, higher optical purity, less waste streams or any or all of the above.

DETAILED DESCRIPTION OF THE INVENTION

In a first aspect of the present invention there is provided a method for the preparation of a first cyclopeptide comprising a vicinal diol from a second cyclopeptide comprising a vicinal diol wherein the vicinal diol is protected with a boronic acid derivative. In the context of the present invention, a vicinal diol is a compound bearing at least two hydroxyl functional groups that are attached to adjacent carbon atoms. The use of ethyl- and phenylboronic acid as a protecting group for 1,2-diols is well known, for instance from Greene, T. W. and Wuts, P. G. M., Protective Groups in Organic Synthesis (John Wiley & Sons, Inc., New York/Chichester/Brisbane/Toronto/Singapore, $2^{nd}$ Ed., 1991, ISBN 0-471-62301-6). In addition, the use of phenylboronic acid in cyclopeptide chemistry has been described in U.S. Pat. No. 5,936,062. In the present invention, approaches alternative to the use of phenylboronic acid were investigated in order to solve several problems associated with phenylboronic acid such as sub-optimal yields and toxicity of the phenylboronic acid which is eventually released in the waste stream. It was found that substituted boronic acids other than phenylboronic acid or naphthylboronic acid are suitable protecting groups for vicinal diols in cyclopeptides. Notably cyclohexylboronic acid and 4-tert-butylphenylboronic acid, both unmentioned in the major textbook in the art by Greene and Wuts, described above.

The suitability of cyclohexylboronic acid is particularly surprising as the skilled person would preferably look for alternate compounds bearing a chromophore (such as tolyl, naphthyl or phenyl) as chromophoric compounds greatly facilitate analysis during research and production activities. Cyclohexyl boronic acid does not have such a chromophore thereby making it a non-obvious choice. Moreover, to the best of our knowledge cyclohexylboronic acid is not suggested in any means in the art in question.

In a first embodiment there is disclosed a method for the preparation of a compound of general formula (1) or a salt thereof comprising the steps of treating a compound of general formula (2) wherein $R_1$ in compounds (1) and (2) is $C(O)R_2$ wherein $R_2$ is $C_9$-$C_{21}$ alkyl, $C_9$-$C_{21}$ alkenyl, $C_1$-$C_{10}$ alkoxyphenyl, alkoxynaphthyl or $C_1$-$C_{10}$ alkoxyterphenyl, with a substituted boronic acid, an activating agent and a reducing agent. Preferably $R_1$ is $C(O)(CH_2)_8CH(CH_3)CH_2CH(CH_3)CH_2CH_3$. The steps mentioned above may be carried out in various sequences using various activating agents and reducing agents as known to the skilled person. Preferred activating agents are thiols with general formula $R_3$—SH. More preferably said activating agents are 2-mercaptobenzimidazole, 2-mercaptobenzothiazole, 2-mercapto-1-methylimidazole, 2-mercapto-4-methoxyphenol or thiophenol. The various preferred sequence of steps are outlined in the following embodiments.

In a second embodiment said compound of general formula (2) is first reacted with a substituted boronic acid $R_5$—B(OH)$_2$ to afford a compound of general formula (3) wherein $R_5$ is cyclohexyl, substituted cyclohexyl or substituted phenyl. In a next step, compound (3) is reacted with a compound of general formula $R_3$—SH to afford a compound of general formula (4) with $R_5$ as mentioned above.

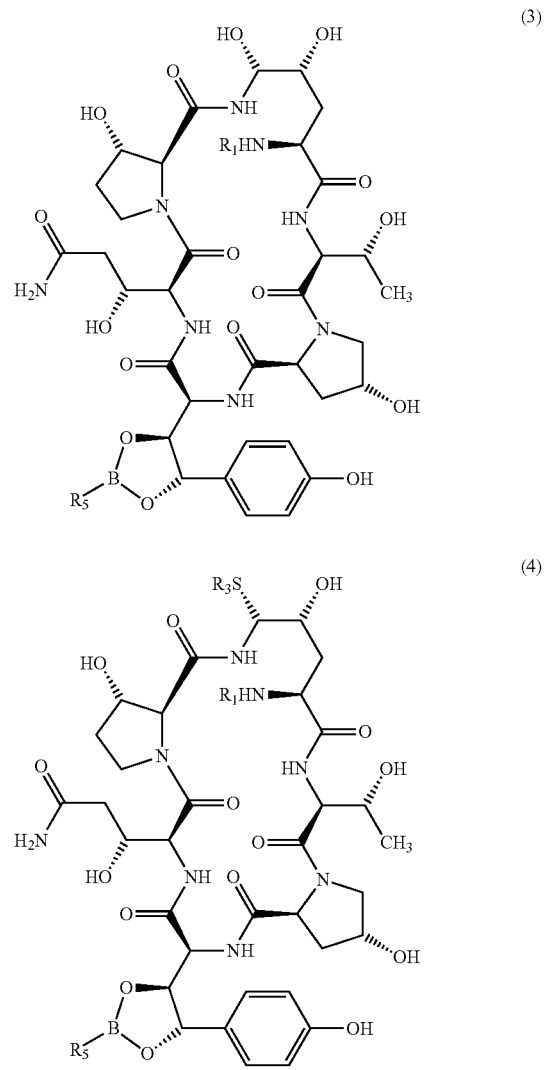

The above conversion may be carried out in a variety of solvents that are inert to the reaction conditions such as (substituted) alkanes, ethers and substituted benzenes, for instance acetonitrile, dichloromethane, diethyl ether, tetrahydrofuran, toluene and the like. Preferably the substituted boronic acid $R_5$—B(OH)$_2$ is cyclohexylboronic acid or 4-tert-butylphenylboronic acid. Preferred temperatures are from −100° C. to 30° C., more preferably from −50° C. to 0° C., most preferably from −20° C. to −5° C. Subsequently, compound (4) is hydrolyzed to afford a compound of general formula (5) which is then reduced to afford a compound of general formula (6);

(5)

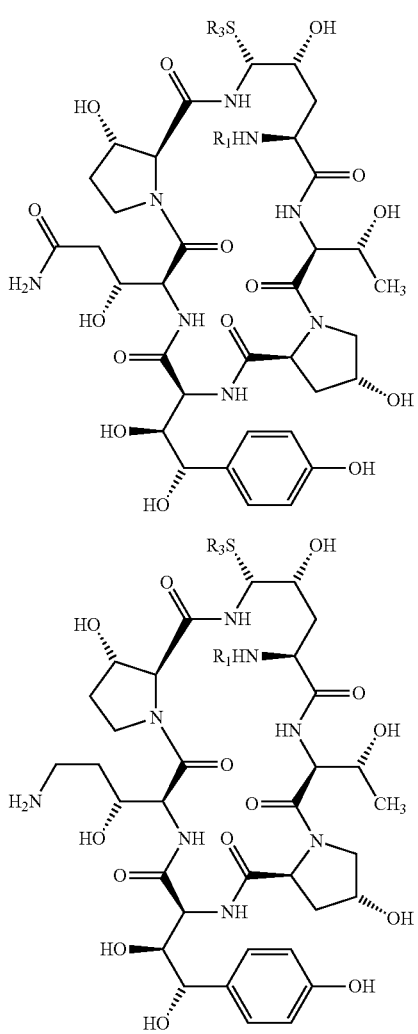

(6)

Finally, compound (6) is converted to said compound of general formula (1) by reaction with ethylenediamine. In W. R. Leonard et al. (J. Org. Chem. 2007, 72, 2335-2343) the formation of the mono-phenylboronate ester of the vicinal hydroxyl groups required, as evidenced from the experimental details, two equivalents of phenylboronic acid. Although it was established that this excess could also be applied in the present invention with a substituted boronic acid, it was surprisingly established that lower amounts of substituted boronic acid were equally or even better suitable thereby reducing the amount of waste. Thus, the preferred ratio, on a molecular basis, of substituted boronic acid to the compound of general formula (1) is from 1.01 to 3, more preferably from 1.05 to 2 and most preferably from 1.1 to 1.5.

In a third embodiment a compound of general formula (2) is first reacted with a substituted boronic acid to afford a compound of general formula (3), which is subsequently reacted with a compound of general formula $R_3$—SH to afford a compound of general formula (4) with $R_5$ as mentioned above. Compound (4) is then reduced and hydrolyzed to afford a compound of general formula (6) which is converted to said compound of general formula (1) by reaction with ethylenediamine.

In a fourth embodiment a compound of general formula (2) is first reacted with a substituted boronic acid to afford a compound of general formula (3) which is subsequently reduced to afford a compound of general formula (7) with $R_5$ as mentioned above. Compound (7) is then reacted with a compound of general formula $R_3$—SH and hydrolyzed to afford a compound of general formula (6) which is converted to said compound of general formula (1) by reaction with ethylenediamine.

(7)

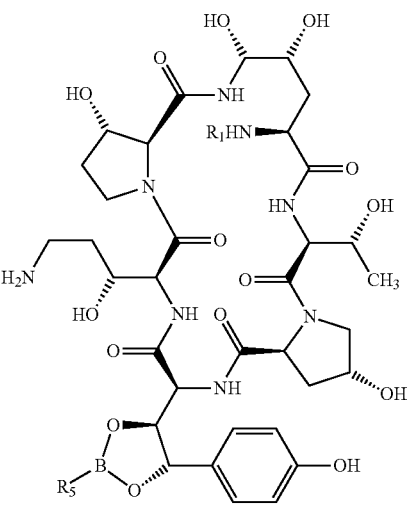

In a fifth embodiment, the compound of general formula (4) described above is first reacted with a silylating agent prior to further conversions. Suitable silylating agents are bis(trimethylsilyl)trifluoroacetamide, tert-butyldimethylsilyl chloride, trimethylsilyl chloride and the like.

In a sixth embodiment said reaction with a substituted boronic acid $R_5$—$B(OH)_2$ that is not phenylboronic acid or naphthylboronic acid is succeeded by and/or combined with reaction with phenylboronic acid. It was surprisingly found that such combination of protecting groups can lead to still more favourable results. Preferably said reaction with phenylboronic acid is carried out after reaction with from 0. to 1.2 equivalents of a substituted boronic acid $R_5$—$B(OH)_2$ that is not phenylboronic acid or naphthylboronic acid In a second aspect of the present invention there is provided a compound of general formula (8)

(8)

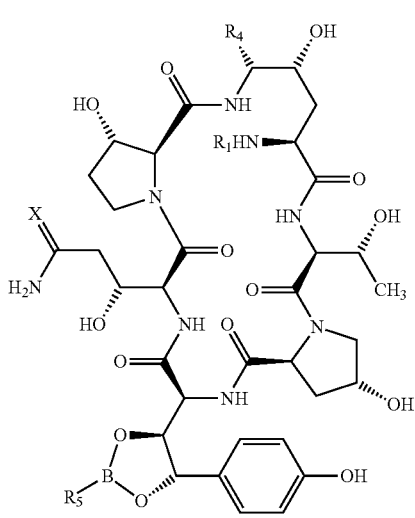

wherein $R_1$ is $C(O)R_2$ wherein $R_2$ is $C_9$-$C_{21}$ alkyl, $C_9$-$C_{21}$ alkenyl, $C_1$-$C_{10}$ alkoxyphenyl, $C_1$-$C_{10}$ alkoxynaphthyl or $C_1$-$C_{10}$ alkoxyterphenyl, wherein $R_4$ is OH or —SR3 wherein $R_3$ is benzimidazol-2-yl, benzothiazol-2-yl, 1-methylimidazol-2-yl, 4-methoxyphenyl or phenyl, wherein $R_5$ is cyclohexyl, substituted cyclohexyl or substituted phenyl and wherein X is O or H,H.

In one embodiment the preferred substituent $R_1$ is $C(O)(CH_2)_8CH(CH_3)CH_2CH(CH_3)CH_2CH_3$ which is the substituent present in the antifungal agent caspofungin.

In another embodiment the preferred substituent $R_4$ is OH or —S-phenyl. In yet another embodiment the preferred substituent $R_5$ is cyclohexyl or 4-tert-butylphenyl.

In a third aspect of the invention there is provided the use of a substituted boronic acid in the preparation of a cyclopeptide bearing a vicinal diol. Protection of diols with substituted boronic acids is not limited to the compound of the first embodiment of the first aspect of the present invention but can also be applied to similar cyclopeptides containing a vicinal diol system. In a preferred embodiment the cyclopeptide is anidulafungin, caspofungin, cilofungin or micafungin.

EXAMPLES

General

Pneumocandin was obtained by fermentation of *Glarea Lozoyensis* (*Zalerion arboricola*) as described in WO 2000/008197. Commercially available reagents were used as received unless mentioned otherwise. Solvents were dried over 3 Å molecular sieves. HPLC analysis was carried out using a Waters XBridge C18 column, 3.5 µm, 150 mm×2.1 mm under the following conditions:

Injection volume: 5 µL
Detection: UV (210 and 270 nm)
Flow: 0.40 ml/min
Column temp: 25° C.
Mobile phase A: 50 mM $K_2HPO_4$+acetonitrile (6:4); pH 6.0
Mobile phase B: 75% acetonitrile
Gradient:

| Time (min) | 0 | 1.5 | 5.0 | 7.0 | 7.5 | 11 |
|---|---|---|---|---|---|---|
| % A | 100 | 100 | 0 | 0 | 100 | 100 |
| % B | 0 | 0 | 100 | 100 | 0 | 0 |

Retention times (all with $R_1$=$C(O)(CH_2)_8CH(CH_3)CH_2CH(CH_3)CH_2CH_3$): 1: 2.5 min; 2: 5.8 min; 6 ($R_3$=phenyl): 6.4 min; 5 ($R_3$=phenyl): 7.3 min.

Example 1

Pneumocandin cyclohexylboronate ester using 2.0 equiv. cyclohexylboronic acid (8; $R_1$=$C(O)(CH_2)_8CH(CH_3)CH_2CH(CH_3)CH_2CH_3$;
$R_4$=OH; $R_5$=cyclohexyl; X=O)

Under $N_2$ finely divided pneumocandin $B_0$ (0.68 g, assay total pneumocandins 95%, assay pneumocandin $B_0$ and $C_0$ 81%; 0.61 mmol pneumocandins) and cyclohexylboronic acid (156 mg, 1.22 mmol) were added to acetonitrile (20 ml, pre-dried on molecular sieves of 3 Å).

Example 2

Pneumocandin phenylthioaminal cyclohexylboronate ester (8; $R_1$=$C(O)(CH_2)_8CH(CH_3)CH_2CH(CH_3)CH_2CH_3$;
$R_4$=S-phenyl; $R_5$=cyclohexyl; X=O)

To the suspension obtained in Example 1 thiophenol (190 µl, 1.86 mmol) was added. The suspension was cooled and maintained at −15° C. and trifluoromethanesulfonic acid (163 µL, 1.83 mmol) was added and the reaction mixture was maintained at −15° C. for 20 h under nitrogen. The conversion was followed by HPLC: sample after 3 h (50 µl reaction mixture+20 µl 0.85 M sodium acetate+0.88 ml methanol): conversion was 79%; after 20 h the conversion was 97%.

Example 3

Pneumocandin phenylthioaminal (5; $R_1$=$C(O)(CH_2)_8CH(CH_3)CH_2CH(CH_3)CH_2CH_3$;
$R_3$=phenyl)

The reaction mixture obtained in Example 2 was quenched with 0.844 M sodium acetate trihydrate (2.2 ml; 1.86 mmol). The suspension was warmed to 17° C., maintained for 2 h, and cooled to 0° C. and stirred at 0° C. overnight, during which the concentration of the title compound in the mother-liquor decreased from 2.1 to 1.6 g/l. The precipitate was filtered off, washed with 90% acetonitrile (3×10 ml), and dried under vacuum at 30° C., giving 0.53 g of the title compound as an off-white powder with an HPLC-assay of 87%. Isolated yield (over $B_0$ and $C_0$): 77%. Loss to mother liquor: 44 ml; 1.4 g/l; 10%.

Example 4

Pneumocandin cyclohexylboronate ester using 1.1 equiv. cyclohexylboronic acid (8; $R_1$=$C(O)(CH_2)_8CH(CH_3)CH_2CH(CH_3)CH_2CH_3$;
$R_4$=OH; $R_5$=cyclohexyl; X=O)

Under nitrogen finely divided pneumocandin $B_0$ (0.68 g, assay total pneumocandins 95%, assay pneumocandin ($B_0$ and $C_0$) 81%; 0.61 mmol pneumocandins) and cyclohexylboronic acid (86 mg, 0.67 mmol) were added to acetonitrile (20 ml, pre-dried on molecular sieves of 3 Å).

Example 5

Pneumocandin phenylthioaminal cyclohexylboronate ester (8; $R_1$=$C(O)(CH_2)_8CH(CH_3)CH_2CH(CH_3)CH_2CH_3$;
$R_4$=S-phenyl; $R_5$=cyclohexyl; X=O)

To the suspension obtained in Example 4 thiophenol (190 µl, 1.86 mmol) was added. The suspension was cooled and maintained at −15° C. and trifluoromethanesulfonic acid (163 µL, 1.83 mmol) was added and the reaction mixture was maintained at −15° C. for 20 h under nitrogen after which the conversion was determined with HPLC (50 µl reaction mixture+20 µl 0.85 M sodium acetate+0.88 ml methanol) to be 99%.

Example 6

Pneumocandin phenylthioaminal (5; $R_1$=C(O)(CH$_2$)$_8$CH(CH$_3$)CH$_2$CH(CH$_3$)CH$_2$CH$_3$;
$R_3$=phenyl)

The reaction mixture obtained in Example 5 was quenched with 0.844 M sodium acetate trihydrate (2.2 ml; 1.86 mmol). The suspension was warmed to 17° C., maintained overnight, and cooled to 0° C. and stirred at 0° C. for 3 h. The precipitate was filtered off, washed with 90% acetonitrile of 0° C. (3×8 ml), and dried under vacuum at 30° C., giving 0.51 g of the title compound as an off-white powder with an HPLC-assay of 90%. Isolated yield (over $B_0$ and $C_0$): 77%.

Example 7

Pneumocandin phenylthioaminal amine (6; $R_1$=C(O)(CH$_2$)$_8$CH(CH$_3$)CH$_2$CH(CH$_3$)CH$_2$CH$_3$;
$R_3$=phenyl) using BSTFA (3 equiv.)

Under nitrogen phenylthioaminal (5; $R_1$=C(O)(CH$_2$)$_8$CH(CH$_3$)CH$_2$CH(CH$_3$)CH$_2$CH$_3$; $R_3$=phenyl; 0.56 g; 0.32 mmol; assay 67% by NMR) was suspended in dry THF (30 ml). At 20° C. bis(trimethylsilyl)trifluoroacetamide (BSTFA, 0.26 ml; 0.97 mmol) was added and the mixture was stirred for 2 h at 20° C. under nitrogen. The solution was cooled to −2° C. and 1 M BH$_3$.THF (2.25 ml; 2.25 mmol) was added. The solution was stirred at ∼−2° C. overnight. A sample of 3 ml was taken which was quenched with 2 M HCl (200 µl): conversion 24%. Another portion of 1 M BH$_3$.THF (0.75 ml; 0.75 mmol) was added and stirring at −2° C. was continued for 24 h. The reaction mixture was quenched with 2 M HCl (2 ml; 4 mmol). Hydrogen gas evolved from the mixture. This solution was stirred at 0° C. for 2 h and analyzed by HPLC: conversion 34%.

Example 8

Pneumocandin phenylthioaminal amine (6; $R_1$=C(O)(CH$_2$)$_8$CH(CH$_3$)CH$_2$CH(CH$_3$)CH$_2$CH$_3$;
$R_3$=phenyl) using BSTFA (4 equiv.)

Under nitrogen phenylthioaminal (5; $R_1$=C(O)(CH$_2$)$_8$CH(CH$_3$)CH$_2$CH(CH$_3$)CH$_2$CH$_3$; $R_3$=phenyl; 0.56 g; 0.32 mmol; assay 67% by NMR) was suspended in dry THF (30 ml). At 20° C. BSTFA (0.34 ml; 1.27 mmol) was added and the mixture was stirred for 2 h at 20° C. under nitrogen. The solution was cooled to −2° C. and 1 M BH$_3$.THF (2.25 ml; 2.25 mmol) was added. The solution was stirred at ∼−2° C. overnight. A sample of 3 ml was taken which was quenched with 2 M HCl (200 µl): conversion 28%. Another portion of 1 M BH$_3$.THF (0.75 ml; 0.75 mmol) was added and stirring at −2° C. was continued for 24 h. The reaction mixture was quenched with 2 M HCl (2 ml; 4 mmol). Hydrogen gas evolved from the mixture. This solution was stirred at 0° C. for 2 h and analyzed by HPLC: conversion 41%.

Example 9

Pneumocandin phenylthioaminal amine (6; $R_1$=C(O)(CH$_2$)$_8$CH(CH$_3$)CH$_2$CH(CH$_3$)CH$_2$CH$_3$; $R_3$=phenyl) using BSTFA (5 equiv.)

Under nitrogen phenylthioaminal (5; $R_1$=C(O)(CH$_2$)$_8$CH(CH$_3$)CH$_2$CH(CH$_3$)CH$_2$CH$_3$; $R_3$=phenyl; 0.56 g; 0.32 mmol; assay 67% by NMR) was suspended in dry THF (30 ml). At 20° C. BSTFA (0.43 ml; 1.60 mmol) was added and the mixture was stirred for 1 h at 20° C. under nitrogen. The solution was cooled to −3.5° C. and 1 M BH$_3$.THF (2.24 ml; 2.24 mmol) was added. The temperature rose to −3° C. and the solution was stirred at ∼−3° C. overnight. It was quenched with 2 M HCl (2 ml; 4 mmol). Hydrogen gas evolved from the mixture. This solution was stirred at 0° C. for 2.5 h and analyzed by HPLC: conversion 32%.

Example 10

Pneumocandin phenylthioaminal amine cyclohexylboronate ester (8; $R_1$=C(O)(CH$_2$)$_8$CH(CH$_3$)CH$_2$CH(CH$_3$)CH$_2$CH$_3$;
$R_4$=S-phenyl; $R_5$=cyclohexyl; X=H, H) using cyclohexylboronic acid and BSTFA Under nitrogen phenylthioaminal (5; $R_1$=C(O)(CH$_2$)$_8$CH(CH$_3$)CH$_2$CH(CH$_3$)CH$_2$CH$_3$; $R_3$=phenyl; 0.40 g; 0.23 mmol; assay 66% by NMR) was suspended in dry THF (25 ml). Cyclohexylboronic acid (33 mg; 0.26 mmol) was added. The mixture was heated to reflux. THF was distilled off and the volume was maintained by replenishment with dry THF. The temperature of the reaction mixture rose from 65.4 to 66.3° C. After 1.5 h the mixture (20 ml) was cooled to 20° C. in 1 h. BSTFA (183 µl; 11; 0.68 mmol) was added and the mixture was stirred for 1 h at 20° C. under nitrogen. The solution was cooled to −2° C. in 2 h and 1 M BH$_3$.THF (1.6 ml; 1.6 mmol) was added. The solution was stirred at ∼−2° C. overnight. A sample of 1 ml was taken which was quenched with 2 M HCl (67 µl): conversion 83%. Another portion of 1 M BH$_3$.THF (0.45 ml; 0.45 mmol) was added and stirring at −2° C. was continued for 3 hours.

Example 11

Pneumocandin phenylthioaminal amine (6; $R_1$=C(O)(CH$_2$)$_8$CH(CH$_3$)CH$_2$CH(CH$_3$)CH$_2$CH$_3$;
$R_3$=phenyl)

The reaction mixture obtained in Example 10 was quenched with 2 M HCl (1.4 ml; 2.8 mmol). Hydrogen gas evolved from the mixture. This solution was stirred at 0° C. for 2 h and analyzed by HPLC: conversion 83%.

Example 12

Comparison of cyclohexylboronic acid (CHBA), phenylboronic acid (PBA) and 4-tert-butylphenylboronic acid (TBPBA) in the synthesis of pneumocandin phenylthioaminal (5; $R_1$=C(O)(CH$_2$)$_8$CH(CH$_3$)CH$_2$CH(CH$_3$)CH$_2$CH$_3$;
$R_3$=phenyl)

Several combinations of cyclohexylboronic acid (CHBA), phenylboronic acid (PBA) and 4-tert-butylphenylboronic acid (TBPBA) were investigated in time on conversion, yield and formation of so-called bis-adducts (products having a second thiophenol moiety).
12.1: 2 equiv. PBA Under nitrogen finely divided 2 (CAS0902/187; 1 g, assay total pneumocandins 100%, 0.94 mmol pneumocandins) and phenylboronic acid (PBA; 115 mg, 0.94 mmol), were added to 30 ml dry acetonitrile (<30 ppm water) and the mixture was stirred at RT for 60 min. PBA (115 mg; 0.94 mmol) was added, followed by thiophenol (290 µl, 2.84 mmol) and the suspension was cooled to −15° C. At −15° C. triflic acid (250 µl, 2.82 mmol) was added and the reaction mixture was stirred at −15° C. for 26 h.

| Time (h) | Conversion (%) | Bis-adducts/5 | Yield (%) |
|---|---|---|---|
| 0.5 | 50.4 | 0.99 | 50.2 |
| 1 | 62.2 | 0.96 | 61.8 |
| 1.5 | 71.1 | 0.97 | 70.6 |
| 2 | 76.5 | 1.05 | 75.9 |
| 3 | 83.4 | 1.20 | 82.5 |
| 4 | 88.3 | 1.25 | 87.3 |
| 6 | 95.3 | 1.44 | 94.0 |
| 9 | 98.6 | 1.72 | 96.9 |
| 19 | 99.9 | 2.58 | 97.3 |
| 26 | 100 | 3.38 | 96.6 |

12.2: 1 equiv. PBA and 1 equiv. CHBA

Under nitrogen finely divided 2 (1 g, 0.94 mmol pneumocandins) and CHBA (120 mg, 0.94 mmol), were added to 30 ml dry acetonitrile (<30 ppm water) and the mixture was stirred at RT for 60 min. PBA (115 mg; 0.94 mmol) was added, followed by thiophenol (290 µl, 2.84 mmol) and the suspension was cooled to −15° C. At −15° C. triflic acid (250 µl, 2.82 mmol) was added and the reaction mixture was stirred at −15° C. for 26 h.

| Time (h) | Conversion (%) | Bis-adducts/5 | Yield (%) |
|---|---|---|---|
| 0.5 | 44.5 | 1.71 | 44.2 |
| 1 | 52.7 | 1.71 | 52.2 |
| 1.5 | 59.4 | 1.63 | 58.8 |
| 2 | 63.5 | 1.63 | 62.8 |
| 3 | 69.8 | 1.58 | 69.0 |
| 4 | 75.0 | 1.60 | 74.1 |
| 6 | 81.8 | 1.66 | 80.7 |
| 9 | 87.1 | 1.79 | 85.7 |
| 19 | 93.4 | 2.31 | 91.4 |
| 26 | 95.5 | 2.57 | 93.2 |

12.3: 1 equiv. PBA and 1 equiv. TBPBA

Under nitrogen finely divided 2 (1 g, 0.94 mmol pneumocandins) and TBPBA (167 mg, 0.94 mmol), were added to 30 ml dry acetonitrile (<30 ppm water) and the mixture was stirred at RT for 60 min. PBA (115 mg; 0.94 mmol) was added, followed by thiophenol (290 µl, 2.84 mmol) and the suspension was cooled to −15° C. At −15° C. triflic acid (250 µl, 2.82 mmol) was added and the reaction mixture was stirred at −15° C. for 26 h.

| Time (h) | Conversion (%) | Bis-adducts/5 | Yield (%) |
|---|---|---|---|
| 0.5 | 48.8 | 1.38 | 48.5 |
| 1 | 59.1 | 1.25 | 58.7 |
| 1.5 | 66.5 | 1.26 | 65.9 |
| 2 | 71.4 | 1.28 | 70.7 |
| 3 | 76.4 | 1.45 | 75.6 |
| 4 | 80.8 | 1.45 | 79.8 |
| 6 | 87.3 | 1.57 | 86.1 |
| 9 | 91.2 | 1.82 | 89.7 |
| 19 | 97.2 | 2.59 | 94.8 |
| 26 | 98.3 | 2.80 | 95.6 |

12.4: 1.2 equiv. CHBA

Under nitrogen finely divided 2 (1 g, 0.94 mmol pneumocandins) and CHBA (144 mg, 1.13 mmol), were added to 30 ml dry acetonitrile (<30 ppm water) and the mixture was stirred at RT for 60 min. Thiophenol (290 µl, 2.84 mmol) was added and the suspension was cooled to −15° C. At −15° C. triflic acid (250 µl, 2.82 mmol) was added and the reaction mixture was stirred at −15° C. for 26 h.

| Time (h) | Conversion (%) | Bis-adducts/5 | Yield (%) |
|---|---|---|---|
| 0.5 | 62.4 | 1.67 | 61.7 |
| 1 | 68.0 | 1.85 | 67.1 |
| 1.5 | 74.7 | 1.91 | 73.6 |
| 2 | 78.3 | 1.95 | 77.1 |
| 3 | 83.5 | 2.10 | 82.0 |
| 4 | 87.7 | 2.37 | 85.8 |
| 6 | 92.9 | 2.57 | 90.6 |
| 9 | 95.9 | 2.99 | 93.2 |
| 19 | 97.9 | 4.70 | 93.4 |
| 26 | 98.0 | 5.70 | 92.6 |

12.5: 1.2 equiv. TBPBA

Under nitrogen finely divided 2 (1 g, 0.94 mmol pneumocandins) and TBPBA (200 mg, 1.13 mmol), were added to 30 ml dry acetonitrile (<30 ppm water) and the mixture was stirred at RT for 60 min. Thiophenol (290 µl, 2.84 mmol) was added and the suspension was cooled to −15° C. At −15° C. triflic acid (250 µl, 2.82 mmol) was added and the reaction mixture was stirred at −15° C. for 26 h.

| Time (h) | Conversion (%) | Bis-adducts/5 | Yield (%) |
|---|---|---|---|
| 0.5 | 70.6 | 1.92 | 69.6 |
| 1 | 76.2 | 2.11 | 75.0 |
| 1.5 | 78.1 | 2.34 | 76.6 |
| 2 | 79.4 | 2.51 | 77.8 |
| 3 | 80.4 | 2.77 | 78.6 |
| 4 | 81.9 | 2.98 | 79.9 |
| 6 | 85.2 | 3.40 | 82.7 |
| 9 | 91.3 | 3.86 | 88.1 |
| 19 | 96.9 | 5.11 | 92.1 |
| 26 | 98.1 | 5.82 | 92.5 |

12.6: 2 equiv. CHBA

Under nitrogen finely divided 2 (1 g, 0.94 mmol pneumocandins) and cyclohexylboronic acid (CHBA; 86 mg, 0.67 mmol), were added to 20 ml dry acetonitrile and the mixture was for 60 min. Next thiophenol (190 µl, 1.86 mmol) was added and the suspension was cooled to −15° C. At −15° C. triflic acid (163 µl, 1.84 mmol) was added and the reaction mixture was stirred at −15° C. for 20 h.

| Time (h) | Conversion (%) | Bis-adducts/5 | Yield (%) |
|---|---|---|---|
| 3 | 54.2 | 0.24 | 54.1 |
| 20 | 86.2 | 2.27 | 84.5 |

12.7: 2 equiv. TBPBA

Under nitrogen finely divided 2 (1 g, 0.94 mmol pneumocandins) and cyclohexylboronic acid (CHBA; 120 mg, 0.67 mmol), were added to 20 ml dry acetonitrile and the mixture was for 60 min. Next thiophenol (190 µl, 1.86 mmol) was added and the suspension was cooled to −15 ° C. At −15° C. triflic acid (163 µl, 1.84 mmol) was added and the reaction mixture was stirred at −15° C. for 20 h.

| Time (h) | Conversion (%) | Bis-adducts/5 | Yield (%) |
|---|---|---|---|
| 3 | 76.7 | 1.27 | 75.9 |
| 20 | 94.1 | 3.04 | 91.4 |

Example 13

Pneumocandin phenylthioaminal (5; $R_1$=C(O)(CH$_2$)$_8$CH(CH$_3$)CH$_2$CH(CH$_3$)CH$_2$CH$_3$;
$R_3$=phenyl) using a mixture of cyclohexylboronic acid and phenylboronic acid Under nitrogen finely divided 2 (1.0 g, assay total pneumocandins 100%, 0.94 mmol pneumocandins) and cyclohexylboronic acid (120 mg, 0.94 mmol) were added to 30 ml dry acetonitrile. The mixture was stirred at 35-40° C. for 1 h. After cooling to 20° C. phenylboronic acid (115 mg; 0.94 mmol) and thiophenol (290 µl, 2.84 mmol) were added and the suspension was cooled to −15° C. and triflic acid (250 µL, 2.82 mmol) was added and the reaction mixture was maintained at −15° C. for 20 h. The reaction mixture was quenched with 0.85 M sodium acetate.trihydrate (3.32 ml; 2.8 mmol) and the suspension was maintained at 17° C. for 2 h, cooled to 0° C. and stirred overnight. The precipitate was filtered off, washed three times with 10 ml 90% acetonitrile, and dried under vacuum at 30° C., giving 0.87 g of the title product with a purity of 72.% (HPLC).

Example 14

Pneumocandin phenylthioaminal (5; $R_1$=C(O)(CH$_2$)$_8$CH(CH$_3$)CH$_2$CH(CH$_3$)CH$_2$CH$_3$;
$R_3$=phenyl) using a mixture of 4-tert-butylphenylboronic acid and phenylboronic acid Under nitrogen finely divided 2 (1.0 g, assay total pneumocandins 100%, 0.94 mmol pneumocandins) and 4-tert-butylphenylboronic acid (167 mg, 0.94 mmol) were added to 30 ml dry acetonitrile. The mixture was stirred at 35-40° C. for 1 h. After cooling to 20° C. phenylboronic acid (115 mg; 0.94 mmol) and thiophenol (290 µl, 2.84 mmol) were added and the suspension was cooled to −15° C. and triflic acid (250 µL, 2.82 mmol) was added and the reaction mixture was maintained at −15° C. for 20 h. The reaction mixture was quenched with 0.85 M sodium acetate.trihydrate (3.32 ml; 2.8 mmol) and the suspension was maintained at 17° C. for 2 h, cooled to 0° C. and stirred overnight. The precipitate was filtered off, washed three times with 10 ml 90% acetonitrile, and dried under vacuum at 30° C., giving 0.86 g of the title product with a purity of 74.7% (HPLC).

Example 15

Pneumocandin phenylthioaminal amine (6; $R_1$=C(O)(CH$_2$)$_8$CH(CH$_3$)CH$_2$CH(CH$_3$)CH$_2$CH$_3$;
$R_3$=phenyl) using 4-tert-butylphenylboronic acid and BSTFA (3 equiv.)

Under nitrogen 5 ($R_1$=C(O)(CH$_2$)$_8$CH(CH$_3$)CH$_2$CH(CH$_3$)CH$_2$CH$_3$; $R_3$=phenyl; 3.0 g; 71.7%) was suspended in dry THF (120 ml). 4-tert-Butylphenylboronic acid (0.464 g; 2.6 mmol) was added and the mixture was heated to reflux and azeotropically dried by passing the refluxate through a bed of molecular sieves of 0.3 nm (400 g) until the reaction temperature remained constant (T increased from 67.2 to 67.5° C.). After 4 h the mixture was cooled to 21° C. and BSTFA (1.87 ml; 7.08 mmol) was added and the mixture was stirred for 1 h at 20° C. under nitrogen. The solution was cooled to −10° C. and 1 M BH$_3$.THF (10.65 ml; 10.65 mmol) was added between −12 and −10° C. The solution was stirred at ~−10° C. overnight. The reaction mixture was sampled (0.5 ml reaction mixture+50 µl 2M HCl; diluted with 10 ml methanol) and the conversion was determined with HPLC to be 66%.

The invention claimed is:

1. A compound of the general formula (8)

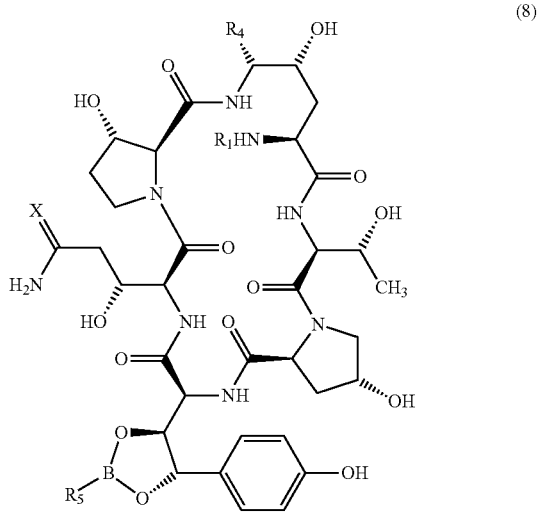

(8)

wherein $R_1$ is C(O)$R_2$, $R_2$ is $C_9$-$C_{21}$ alkyl, $C_9$-$C_{21}$ alkenyl, $C_1$-$C_{10}$ alkoxyphenyl, $C_1$-$C_{10}$ alkoxynaphthyl or $C_1$-$C_{10}$ alkoxyterphenyl, $R_3$ is benzimidazol-2-yl, benzothiazol-2-yl, 1-methylimidazol-2-yl, 4-methoxyphenyl or phenyl, $R_4$ is OH or —SR3, $R_5$ is cyclohexyl, or 4-tert-butylphenyl, X is O or H,H.

2. The compound according to claim 1, wherein $R_1$ is C(O)(CH$_2$)$_8$CH(CH$_3$)CH$_2$CH(CH)CH$_2$CH$_3$.

3. The compound according to claim 1, wherein $R_4$ is OH or —S-phenyl.

* * * * *